United States Patent
Harnisch (10) Patent No.: US 9,763,686 B2
(45) Date of Patent: Sep. 19, 2017

(54) IMPLANT MAGNET INSERTION AND REMOVAL TOOLS

(71) Applicant: MED-EL Elektromedizinische Geraete GmbH, Innsbruck (AT)

(72) Inventor: Andreas Harnisch, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 200 days.

(21) Appl. No.: 14/731,639

(22) Filed: Jun. 5, 2015

(65) Prior Publication Data

US 2015/0359553 A1 Dec. 17, 2015

Related U.S. Application Data

(60) Provisional application No. 62/012,447, filed on Jun. 16, 2014.

(51) Int. Cl.
*A61B 17/30* (2006.01)
*A61N 1/375* (2006.01)
*A61N 1/36* (2006.01)

(52) U.S. Cl.
CPC .......... *A61B 17/30* (2013.01); *A61N 1/36032* (2013.01); *A61N 1/375* (2013.01); *H04R 2460/17* (2013.01)

(58) Field of Classification Search
CPC . A61B 17/30; A61B 17/10; A61B 2017/2926; A61B 2017/00623; A61N 1/36032; A61N 1/0541
See application file for complete search history.

(56) References Cited

U.S. PATENT DOCUMENTS

| 4,437,362 | A | 3/1984 | Hurst |
| 5,002,561 | A | 3/1991 | Fisher |

(Continued)

FOREIGN PATENT DOCUMENTS

| WO | 03092326 A1 | 11/2003 |
| WO | 2014164023 A1 | 10/2014 |

OTHER PUBLICATIONS

International Searching Authority—International Search Report—International Application No. PCT/US2015/034355 dated Sep. 11, 2015, together with the Written Opinion of the International Searching Authority, 10 pages.

(Continued)

*Primary Examiner* — Alexander Orkin
(74) *Attorney, Agent, or Firm* — Sunstein Kann Murphy & Timbers LLP (57) ABSTRACT

A magnet insertion tool for use with an implantable device includes an upper part having an insertion member and an alignment member movably coupled to the insertion member. The insertion member includes a positioning surface configured to position the implantable device between the insertion and alignment members, a magnet socket extending from the positioning surface and configured to hold an implant magnet, and an alignment surface configured to align the implantable device relative to the magnet socket. The alignment member includes an engagement surface configured to engage the implantable device during insertion of the implant magnet. The alignment member is configured to contact a portion of the insertion member such that the engagement surface and the positioning surface are spaced apart from one another. The tool further includes a lower part, movably coupled to the upper part, that has a platform that is configured to move within the magnet socket.

15 Claims, 10 Drawing Sheets

(56) References Cited

U.S. PATENT DOCUMENTS

| | | | |
|---|---|---|---|
| 5,897,507 A | 4/1999 | Kortenbach et al. | |
| 6,308,101 B1 | 10/2001 | Faltys et al. | |
| 8,758,394 B2 | 6/2014 | Zimmerling et al. | |
| 2002/0188316 A1 | 12/2002 | Dingler | |
| 2003/0171787 A1 | 9/2003 | Money et al. | |
| 2003/0181945 A1 | 9/2003 | Opolski et al. | |
| 2004/0138682 A1* | 7/2004 | Onuki | A61B 17/0401 606/144 |
| 2004/0243177 A1 | 12/2004 | Svehla et al. | |
| 2005/0004629 A1 | 1/2005 | Gibson et al. | |
| 2005/0209564 A1* | 9/2005 | Bonner | A61B 17/3478 604/173 |
| 2005/0251160 A1* | 11/2005 | Saadat | A61B 17/0401 606/153 |
| 2006/0163313 A1* | 7/2006 | Larson | A61B 17/064 227/175.1 |
| 2008/0200923 A1* | 8/2008 | Beckman | A61F 9/00781 606/108 |
| 2008/0221641 A1 | 9/2008 | Hochmair et al. | |
| 2009/0099403 A1 | 4/2009 | Zimmerling et al. | |
| 2009/0299217 A1* | 12/2009 | Bleibach | A61B 10/04 600/564 |
| 2010/0069934 A1* | 3/2010 | Bombard | A61B 17/115 606/153 |
| 2011/0040307 A1* | 2/2011 | Ranchod | A61B 17/083 606/142 |

OTHER PUBLICATIONS

International Searching Authority—International Search Report—International Application No. PCT/US2008/079270 dated Jan. 27, 2009, together with the Written Opinion of the International Searching Authority, 10 pages.

* cited by examiner

IMPLANT MAGNET INSERTION AND REMOVAL TOOLS

CROSS REFERENCE TO RELATED APPLICATIONS

The present application claims priority to U.S. Provisional Patent Application No. 62/012,447 filed Jun. 16, 2014, the disclosure of which is incorporated by reference herein in its entirety.

TECHNICAL FIELD

The present invention relates to implantable medical devices, and specifically to tools and techniques for inserting and removing magnets associated with such devices.

BACKGROUND ART

Some implantable medical devices, such as cochlear implant systems, may include subcutaneous magnets which are used to hold in place various external elements such as transmission coils. However, such magnets are not compatible with various medical imaging systems, for example, high field magnetic resonance imaging (MRI). The magnet may, for example, demagnetize or distort the imaging. To perform an MRI on a patient with an implanted magnet, pre-imaging surgery may be required first to remove the magnet, then the actual imaging may be performed, after which another post-imaging surgery is needed to replace the magnet. Besides the inconvenience of this, the actual removal and replacement of the magnet is not trivial. The magnet may be a small disc-shaped or sphere-shaped device which the surgeon may have some difficulty grasping and handling. In one known design, a removable magnet is located in a silicone pocket which has an opening (a lip) at the lateral side of an implant coil, and magnet removal and replacement is accomplished by means of conventional tweezers.

SUMMARY OF EMBODIMENTS

In accordance with one embodiment of the invention, a magnet insertion tool for use with an implantable device includes an upper part having an insertion member and an alignment member movably coupled to the insertion member. The insertion member includes a positioning surface configured to position the implantable device between the insertion and alignment members, a magnet socket extending from the positioning surface and configured to hold an implant magnet, and an alignment surface configured to align the implantable device relative to the magnet socket. The alignment member includes an engagement surface configured to engage the implantable device during insertion of the implant magnet. The alignment member is configured to contact a portion of the insertion member when in a closed position such that the engagement surface and the positioning surface are spaced apart from one another. The tool further includes a lower part, movably coupled to the upper part, that has a platform that is configured to move within the magnet socket.

In some embodiments, the alignment member may further include a centering element configured to align the implantable device relative to the magnet socket. The centering element may have a ring shape. At least a portion of the insertion member may be formed from a ferromagnetic material configured to magnetically hold the implant magnet in the magnet socket. The magnet insertion tool may further include a spring between the upper and lower parts. The spring may be configured to hold the lower part in a starting position so that the platform is biased toward a bottom of the magnet socket. For example, the spring may be a flat spring. The engagement surface and the positioning surface may be spaced apart by a distance that permits the implantable device to be inserted between the engagement and positioning surfaces. The platform may be configured to move from a bottom of the magnet socket to a top of the magnet socket during the insertion of the implant magnet. The lower part may be configured to contact the insertion member when the platform moves to the top of the magnet socket in order to prevent the platform from further upward movement within the magnet socket. The lower part may be movably coupled to the insertion member, e.g., to a middle section of the insertion member. The insertion member may include a securing device configured to hold the insertion member and the alignment member in the closed position. In this case, the alignment member may include a pin and the securing device may be a latch configured to engage the pin. The insertion member may include a tip configured to lift the implantable device away from an implantation site so that the implantable device is positioned between the alignment and insertion members. The alignment surface may have a curved shape. The upper and lower parts may be movably coupled by a joint configured to hold the lower part substantially parallel to the upper part and configured to allow the lower part to move relative to the upper part by up to 90 degrees.

DESCRIPTION OF ILLUSTRATIVE EMBODIMENTS

Embodiments of the present invention are directed to a magnet insertion tool and a magnet removal tool for use with an implantable device. The magnet insertion tool holds the implant magnet when inserting the magnet into an implanted device and the magnet removal tool removes the implant magnet when removing the magnet from the implanted device. Such tools limit the mechanical stress placed on the implanted device and the surrounding tissue, such as the skull, while permitting the size of the incision to be kept relatively small. Appropriate designs help maintain the electrical properties (e.g., inductivity, resistance) and the mechanical integrity of various elements of the implanted device such as a coil assembly (e.g., an optimal fit between the coil assembly and the magnet or magnet housing) and prevent damage to the surrounding tissue. The insertion and removal tools also enable the use of faster, gentle surgical techniques. Details of illustrative embodiments are discussed below.

Figure 1A:
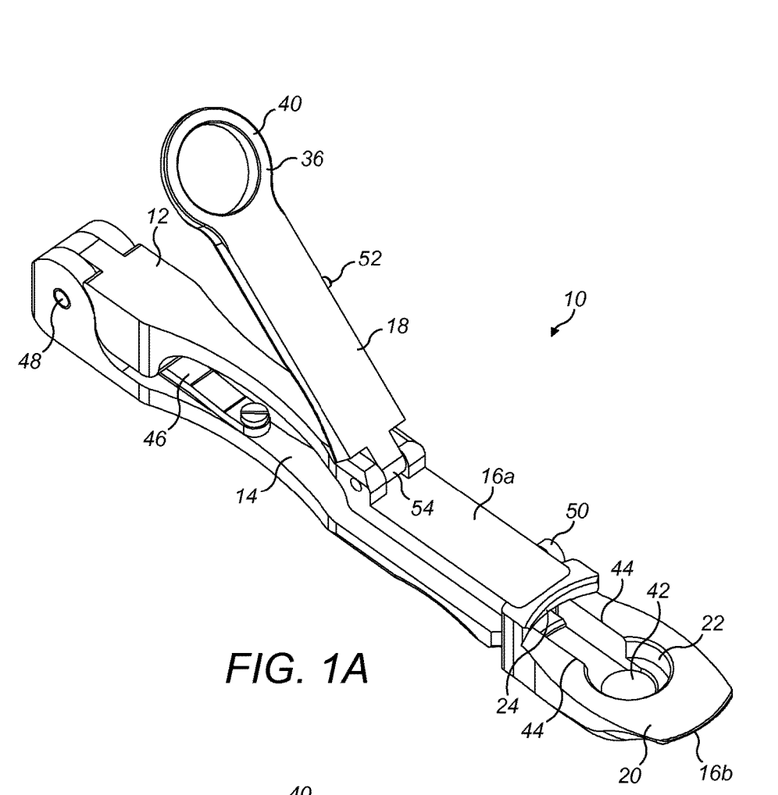
FIGS. 1A and 1B show a perspective top view and a perspective bottom view, respectively, of a magnet insertion tool according to embodiments of the present invention.
Figure 1B:
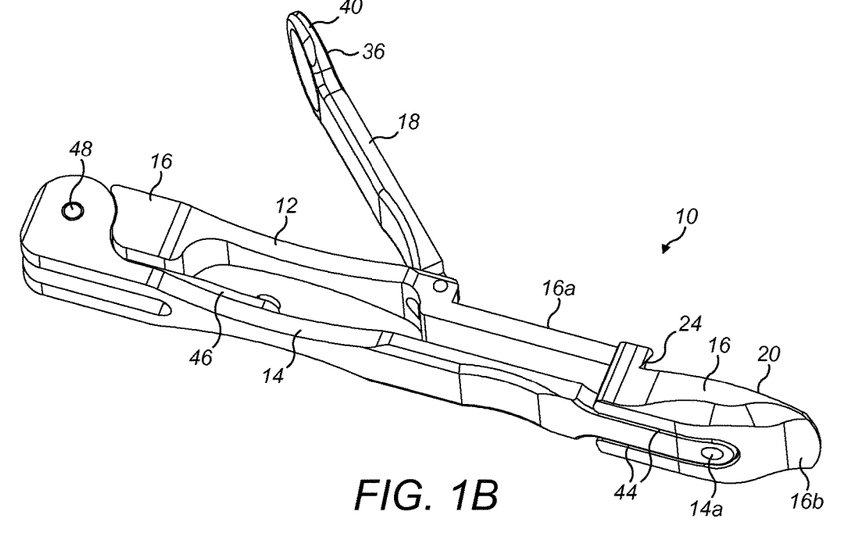
Figure 1C:
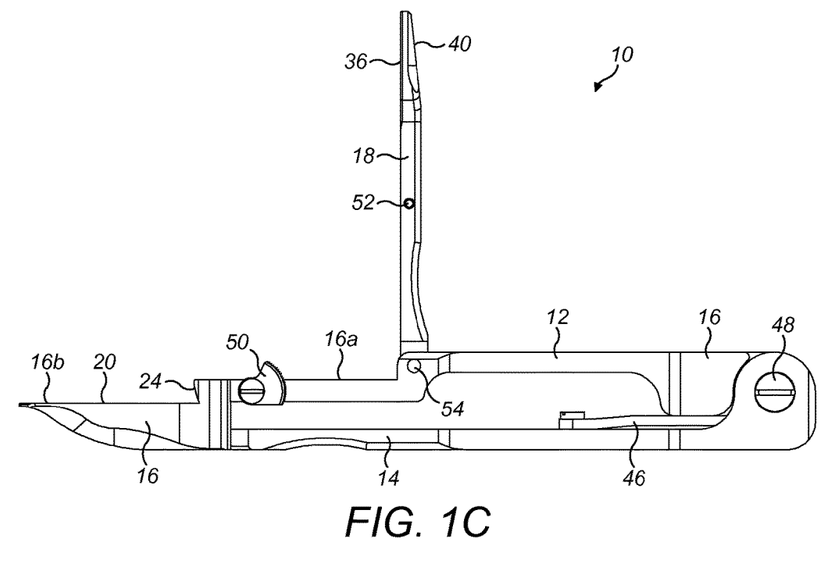
FIGS. 1C and 1D show a side view of a magnet insertion tool in an open and closed position, respectively, according to embodiments of the present invention.
Figure 1D:
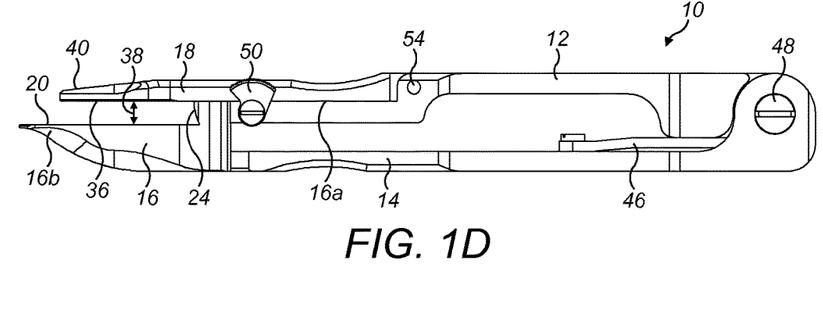

FIGS. 1A-1E show various views of a magnet insertion tool 10 according to embodiments of the present invention. The insertion tool 10 includes an upper part 12 and a lower part 14 that are movably connected to one another. The upper part 12 includes two members, an insertion member 16 and an alignment member 18, movably connected to one another. The insertion member 16 includes a positioning surface 20 configured to position an implantable device (not shown) between the insertion and alignment members 16, 18 when the tool is in a closed position. The insertion member 16 also includes a magnet socket 22, extending down from the positioning surface 20, configured to hold an implant magnet (not shown) and an alignment surface 24 configured to align the implantable device relative to the magnet socket 22 when the implantable device is positioned between the insertion and alignment members 16, 18. FIGS. 1A-1C show the magnet insertion tool 10 in an open position with the alignment member 18 in an upright position, and FIG. 1D shows the insertion tool 10 in a closed position with the alignment member 18 folded down, as described in further detail below.

Figure 2:
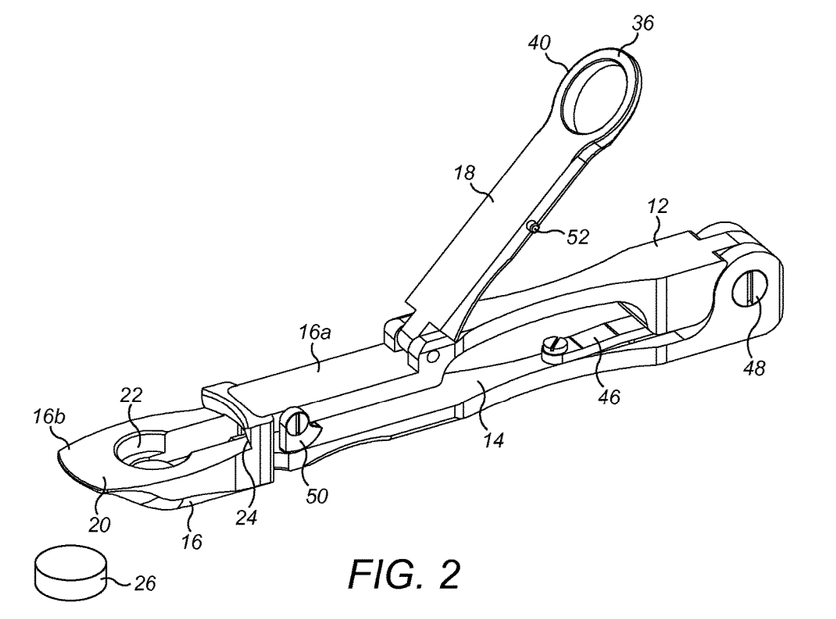
FIGS. 2 and 3 show a perspective view of a magnet insertion tool with a magnet before insertion and after insertion, respectively, into the magnet insertion tool according to embodiments of the present invention.
Figure 3:
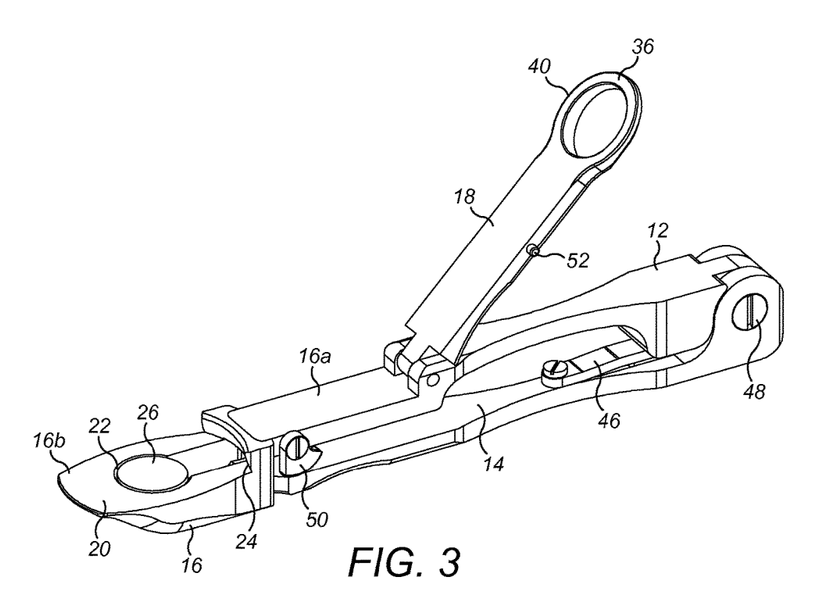

During the tool insertion process, the insertion tool 10 is first placed in the open position, which allows for easy insertion of the implant magnet 26 into the magnet socket 22, such as shown in FIGS. 2 and 3. As shown in FIG. 1D, the insertion tool 10 is then placed in the closed position with the alignment member 18 folded down. The alignment member 18 includes an engagement surface 36 that is configured to engage the implantable device during the magnet insertion process. In the closed position, the alignment member 18 is configured to contact a portion 16a of the insertion member 16 such that the engagement surface 36 and the positioning surface 20 are spaced apart from one another (shown by arrows 38). For example, the engagement surface 36 and the positioning surface 20 are spaced apart by a distance that permits the implantable device to be inserted between the two surfaces 20, 36.

Figure 1E:
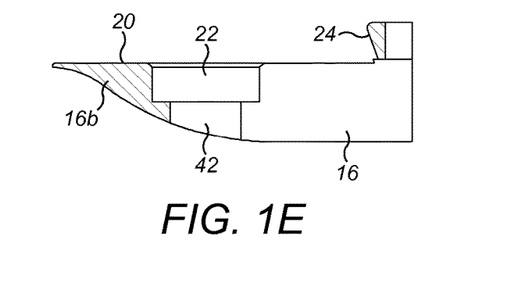
FIG. 1E shows a cross-sectional view of one portion of a magnet insertion tool according to embodiments of the present invention.
Figure 4A:
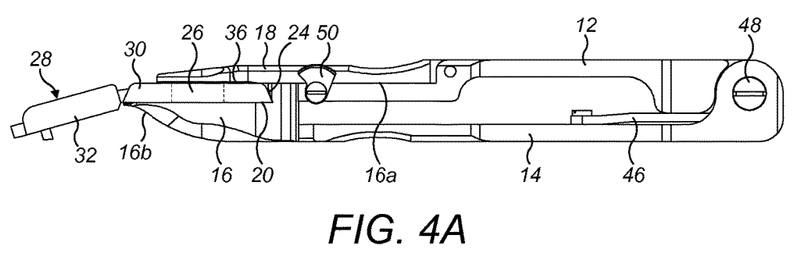
FIGS. 4A and 4B show a side view and a perspective top view, respectively, of a magnet insertion tool with an implantable device inserted between two members of an upper part according to embodiments of the present invention.
Figure 4B:
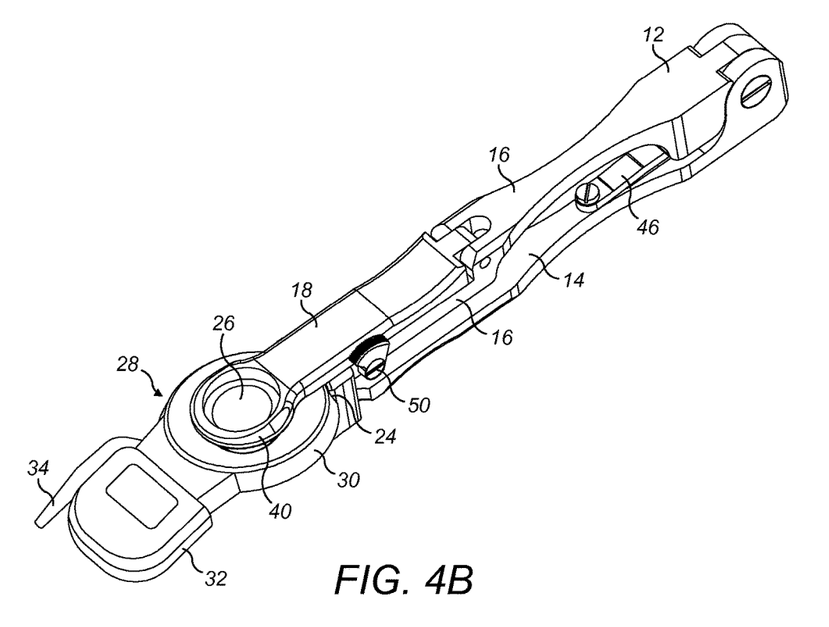

The magnet insertion tool 10 is then inserted underneath a skin flap at an implantation site that contains the implantable device. When in the closed position, the magnet insertion tool 10 has a slim, efficient profile (e.g., thinner than a surgeon's fingers) which enables the surgical incision used for magnet insertion to be as small as possible. The insertion member 16 preferably includes a tip 16b that is configured to lift the implantable device 28, without removing the device 28 from the general implantation site, so that the device 28 is positioned between the alignment member 18 and the insertion member 16 adjacent to the engagement surface 36 and the positioning surface 20, such as shown in FIGS. 4A and 4B. For example, the tip 16b may be rounded with a thinner profile at the edge and a thicker profile near the magnet socket 22, such as shown in FIGS. 1A and 1E.

As shown in FIGS. 4A and 4B, the implantable device 28 may be a portion of a cochlear implant system having a coil housing 30 containing receiving coils for receiving a power and/or data signal from an external transmitting coil (not shown), a stimulator housing 32 attached to the coil housing 30 which contains modules for developing an electrode stimulation signal for stimulating cochlear nerve tissue, and a magnet housing, centered within the coil housing 30, containing an implant magnet 26 that coordinates with a corresponding magnetic element in the external transmitting coil arrangement to hold it in a proper operating position for transferring the signal across the skin into the receiving coils. In the case of a cochlear implant system, an electrode lead 34, connected to the stimulator housing 32, connects to an electrode array (not shown) that applies the stimulation signal to the cochlear nerve tissue.

During the tool insertion, the magnet insertion tool 10 is inserted until the implantable device 28 contacts the alignment surface 24, which properly aligns the implantable device 28 relative to the magnet socket 22 and the implant magnet 26 (e.g., placing the magnet socket concentrically beneath the implant coil housing). The alignment surface 24 may have a curved shape that corresponds to a curved shape of the coil housing 30 to further aid in the alignment. Similarly, the alignment member 18 may include a centering element 40, e.g., a ring-shaped element, towards its end that is configured to align the implantable device 28 relative to the magnet socket 22 (e.g., placing the centering element concentrically above the magnet socket that holds the implant magnet and above the implant coil housing), such as shown in FIG. 4B. The ring-shaped, centering element 40 may have a larger diameter than the diameter of the magnet.

Figure 5:
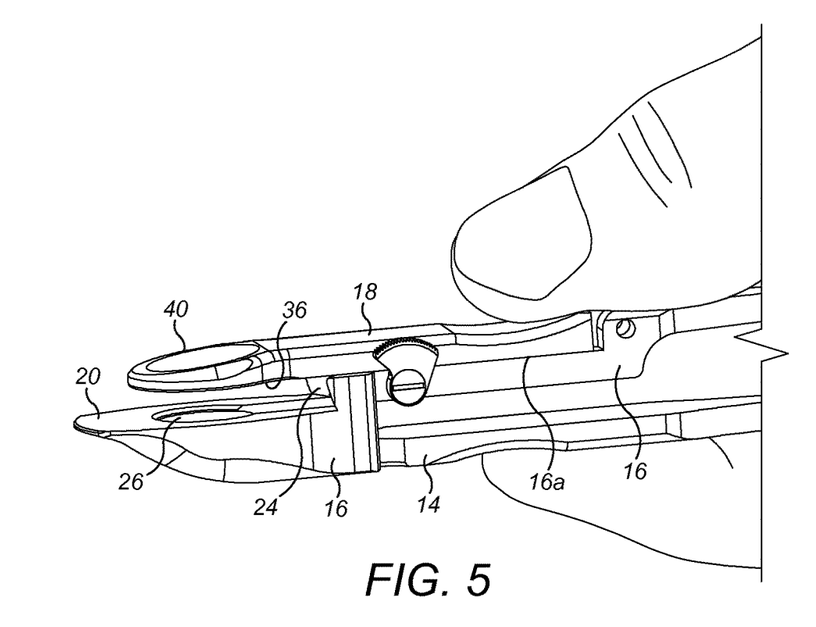
FIGS. 5 and 6 show a side view of a magnet insertion tool in two positions during a magnet insertion process according to embodiments of the present invention.
Figure 6:
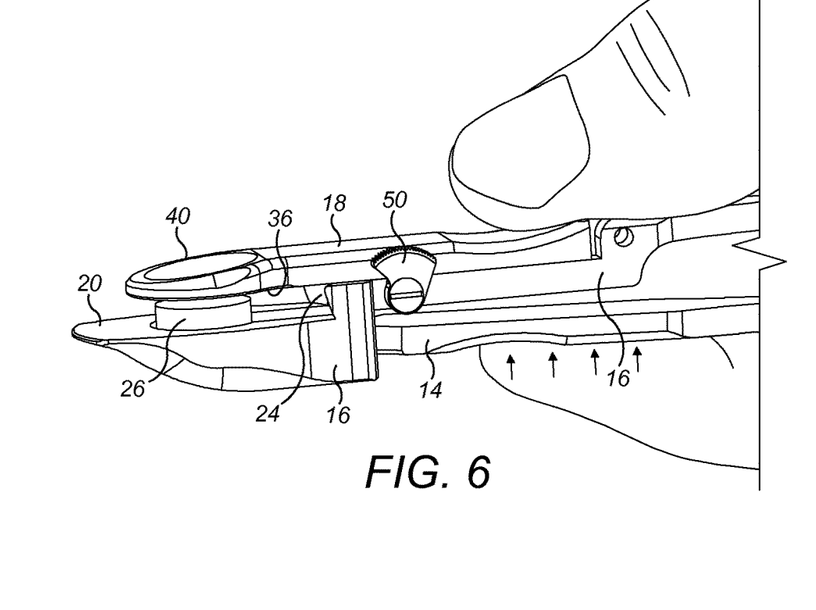

Once the implantable device 28 is properly positioned within the magnet insertion tool 10, a force is applied to the lower part 14 (shown with arrows in FIG. 6) moving the lower part 14 closer to the upper part 12 which causes the implant magnet 26 to be moved within and lifted out of the magnet socket 22 and into the implantable device 28. The upward force may cause the implantable device 28 to engage the engagement surface 36 of the alignment member 18 during the magnet insertion process. The lower part 14 includes a platform 42 that is initially positioned towards a bottom of the magnet socket 22 and is configured to move upward within the magnet socket 22 when the lower part 14 is actuated. FIG. 5 shows the magnet insertion tool 10 with implant magnet 26 in an initial, starting position, and FIG. 6 shows the insertion tool 10 and magnet 26 in a final, magnet insertion position. FIGS. 5 and 6 are shown without the implantable device 28 in order to show the position of the implant magnet 26 more clearly.

As shown in FIGS. 1A and 1B, one portion 14a of the lower part 14, that includes the platform 42, fits within a groove 44 in the insertion member 16. The groove 44 permits the lower part 14 to move upward within the groove 44 and allows the platform 42 to move from a bottom of the magnet socket 22 to a top of the magnet socket 22 during the magnet insertion process. The lower part 14 is configured to contact the insertion member 16 when the platform 42 moves to the top of the magnet socket 22 so that the platform 42 is prevented from further upward movement within the magnet socket 22. This ensures that the magnet insertion tool 10 positions the implant magnet 26 in the same location in the implantable device 28, in a relatively reproducible manner, and the implant magnet 26 is not displaced past the correct magnet position in the implantable device 28.

Preferably, the magnet insertion tool 10 includes a spring 46 positioned between the upper and lower parts 12, 14 that is configured to hold the lower part 14 in the initial, starting position (as shown in FIG. 5) so that the platform 42 is biased toward a bottom of the magnet socket 22 (as shown in FIG. 1E). This allows the insertion tool 10 to return to the starting position without any further effort by a surgeon after the implant magnet 26 is inserted into the implantable device 28. For example, the spring 46 may be a flat spring, as shown in FIGS. 1A-1D, although other springs may also be used as known by those skilled in the art. The spring 46 is preferably positioned towards a joint 48 that movably couples the upper part 12 and lower part 14 together. During the magnet insertion process, the joint is configured to hold the lower part 14 substantially parallel to the upper part 12 while allowing the actuation of the lower part 14.

Figure 7:
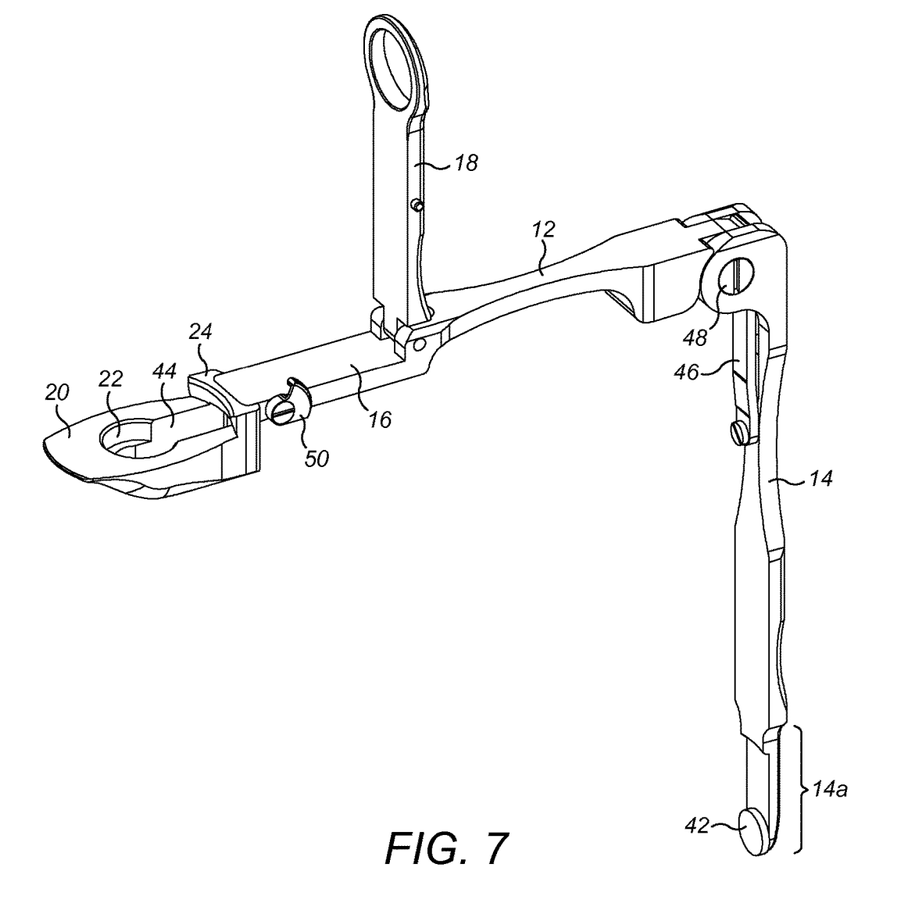
FIG. 7 shows a perspective view of a magnet insertion tool with a lower part in an open position according to embodiments of the present invention.

In some embodiments, all or part of the insertion member 16 (e.g., the magnet socket 22) may be formed from a ferromagnetic material so that the magnet 26 may be mechanically and magnetically held in place in the magnet socket 22 during the tool insertion process. All or part of insertion tool 10 may be formed from appropriate materials, e.g., surgical grade stainless steels. The upper part 12 may also include a securing device 50 configured to hold the insertion member 16 and the alignment member 18 together when the insertion tool 10 is in the closed position. For example, the alignment member 18 may include a pin 52 and the securing device 50 may be a latch configured to engage the pin 52, although other securing mechanisms may also be used as known by those skilled in the art. The securing device 50 prevents the alignment member 18 from opening up during the tool insertion and magnet insertion processes, causing potential complications. Preferably, the alignment member 18 is movably coupled to a middle section of the insertion member 16, e.g., by a hinge 54, but the alignment member 18 may be coupled to the insertion member 16 anywhere along its length As shown in FIG. 7, the joint 48 may allow the lower part 14 of the insertion tool 10 to be opened up to allow easy access to all parts of the insertion tool 10, e.g., for cleaning, disinfecting, steam sterilization, etc. For example, the joint 48 may be configured to allow the lower part 14 to move relative to the upper part 12 by up to an angle of 90 degrees or more.

Figure 8A:
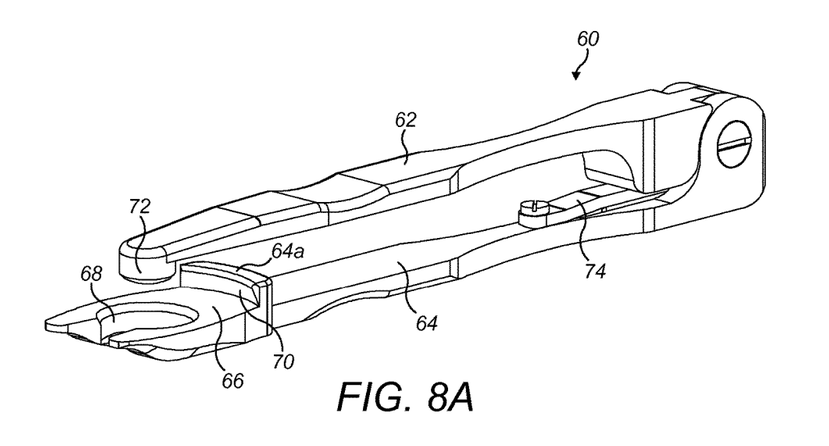
FIGS. 8A-8C show a perspective top view, top view, and side view, respectively, of a magnet removal tool according to embodiments of the present invention.
Figure 8B:
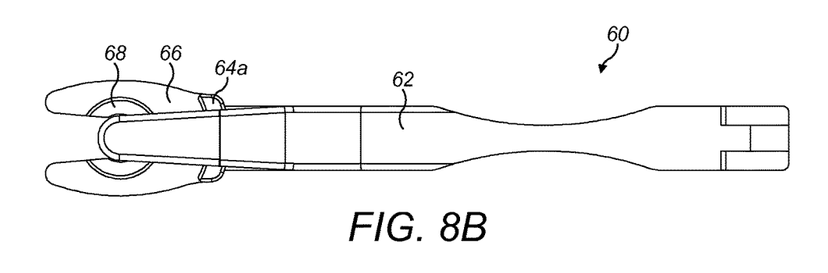
Figure 8C:
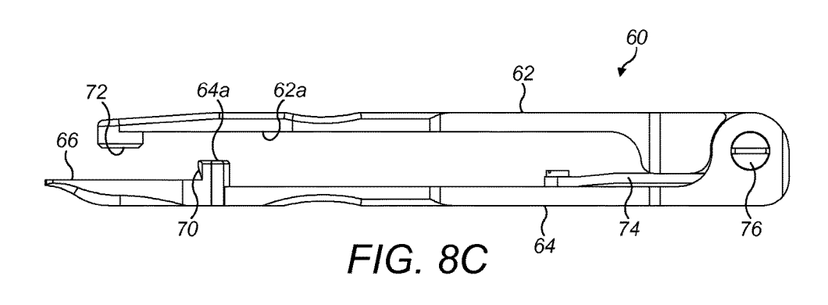
Figure 9:
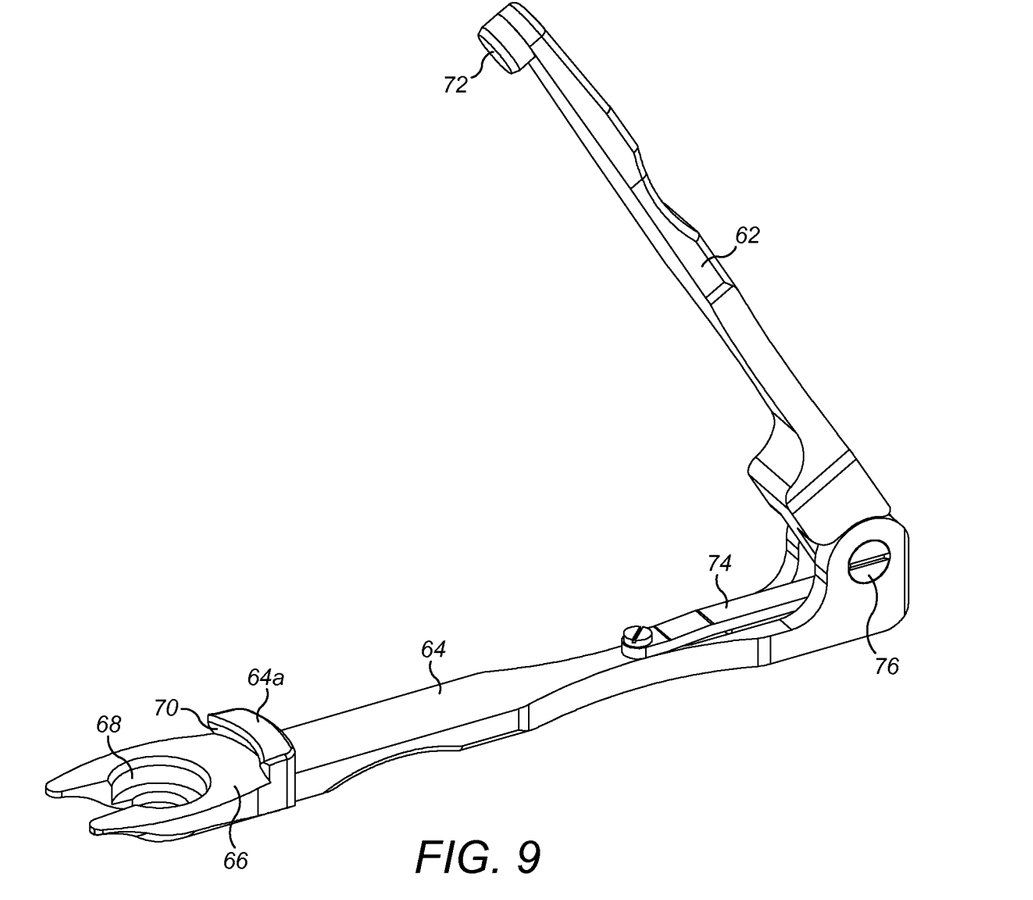
FIG. 9 shows a perspective top view of a magnet removal tool with an upper part in an open position according to embodiments of the present invention.
Figure 10A:
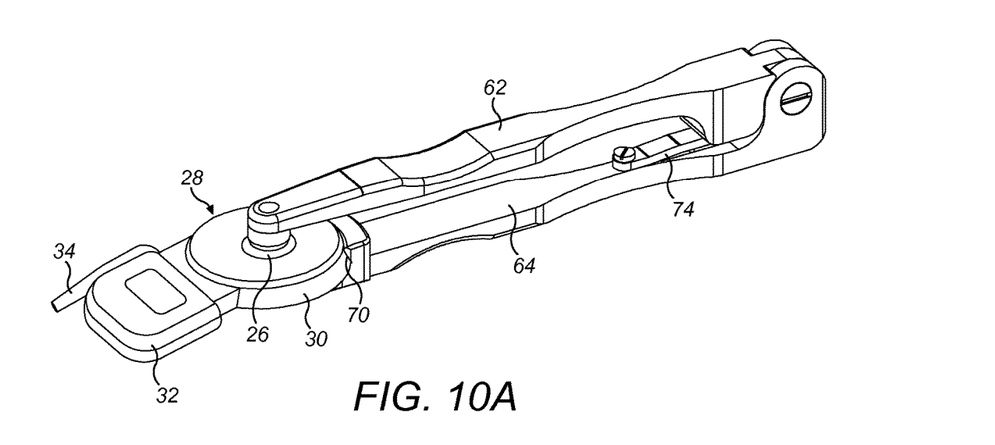
FIGS. 10A and 10B show a perspective top view and side view, respectively, of a magnet removal tool with an implantable device inserted between upper and lower parts according to embodiments of the present invention.
Figure 10B:
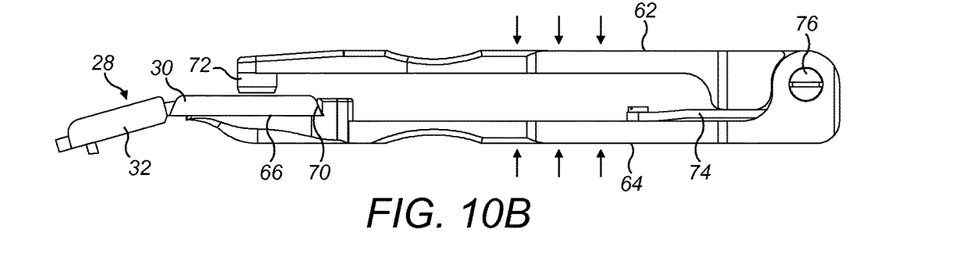
Figure 11:
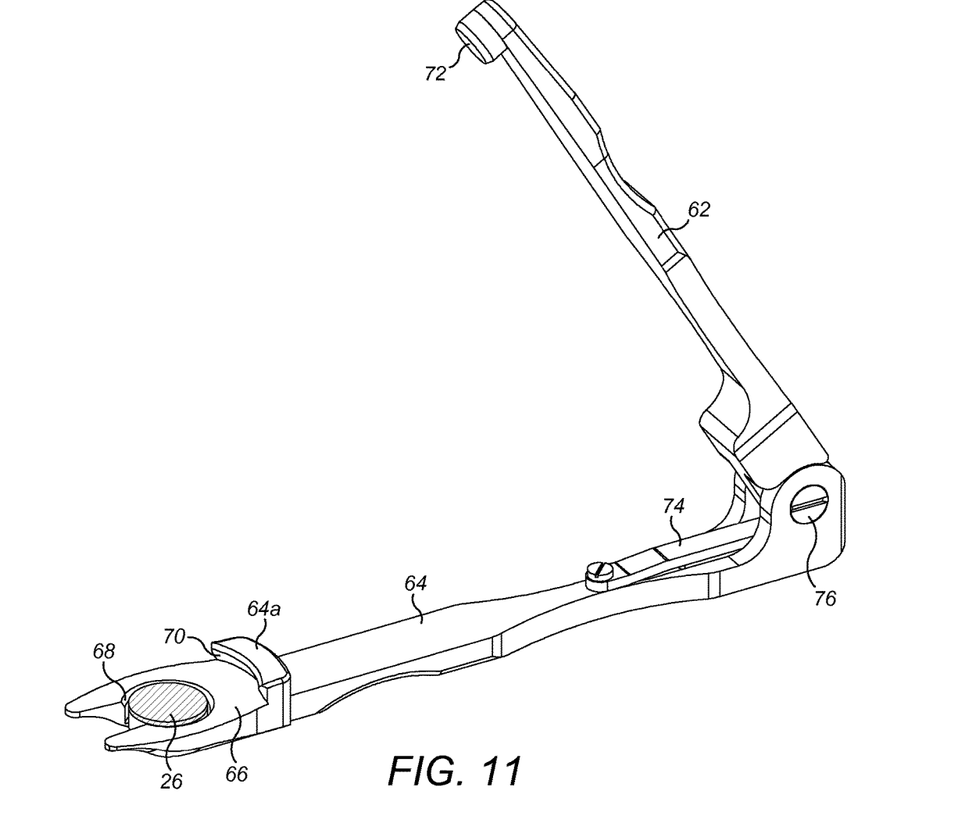
FIG. 11 shows a perspective top view of a magnet removal tool with an upper part in an open position with a magnet removed from an implantable device according to embodiments of the present invention.

FIGS. 8A-8C show various views of a magnet removal tool 60 according to embodiments of the present invention. Similar to the magnet insertion tool 10, the magnet removal tool 60 includes upper and lower parts 62, 64 that are movably connected to one another. The lower part 64 includes a positioning surface 66 configured to position an implantable device 28 between the upper and lower parts 62, 64 when the tool is in a closed position (as shown in FIGS. 10A and 10B). The lower part 64 also includes a magnet socket 68, extending down from the positioning surface 66, configured to hold an implant magnet 26 and an alignment surface 70 configured to align the implantable device 28 relative to the magnet socket 68 when the implantable device is positioned between the upper and lower parts 62, 64. FIGS. 8A-8C show the magnet removal tool 60 in a closed position, and FIGS. 9 and 11 show the removal tool 60 in an open position (e.g., to allow easy access to remove the implant magnet 26 after the magnet removal process or to allow easy access for cleaning, disinfecting, steam sterilization, etc.).

During the tool insertion, the magnet removal tool 60 is inserted underneath a skin flap at an implantation site that contains the implantable device 28. The removal tool 60 is inserted so that the positioning surface 66 is placed under the implantable device 28. The removal tool 60 is inserted into the implantation site until the implantable device 28 contacts the alignment surface 70, which properly aligns the implantable device 28 relative to the magnet socket 68 (e.g., placing the magnet socket concentrically beneath the implant coil housing), such as shown in FIGS. 10A and 10B. The alignment surface 70 may have a curved shape that corresponds to a curved shape of the coil housing 30 to further aid in the alignment.

Once the implantable device 28 is properly positioned within the magnet removal tool 60, a force (shown as arrows in FIG. 10B) is applied to the upper part 62, the lower part 64, or both which causes the two parts 62, 64 to move closer together. Preferably, the upper part 62 includes a platform 72 that protrudes from a bottom surface 62a of the upper part 62 and is configured to only contact the area of the implantable device 28 where the implant magnet 26 is located when the upper and/or lower parts 62, 64 are moved together. This movement causes the platform 72 to push the implant magnet 26 out of the implantable device 28 and into the magnet socket 22 positioned beneath it.

A contact portion 64a of the lower part 64 is configured to contact the upper part 62 when the upper and lower parts 62, 64 are moved together. The contact portion 64a acts as a stopper that prevents the upper and lower parts 62, 64 from coming too close together. This ensures that the magnet removal tool 60 applies a similar amount of force, in a relatively reproducible manner, to the implantable device 28 and the implant magnet 26 with every removal process, and ensures that too much force is not imparted to the implant magnet 26 in the magnet socket 68. FIG. 11 shows the removal tool 60 after the magnet removal process with the implant magnet 26 placed in the magnet socket 68.

Preferably, the magnet removal tool 60 includes a spring 74 positioned between the upper and lower parts 62, 64 that is configured to hold the lower part 64 in an initial, starting position (as shown in FIGS. 10A and 10B) so that the platform 72 is biased away from the implantable device 28. This allows the removal tool 60 to return to this starting position without any further effort by a surgeon after the implant magnet 26 is removed from the implantable device 28. For example, the spring 74 may be a flat spring, as shown in FIGS. 8A and 8C, although other springs may also be used as known by those skilled in the art. The spring 74 is preferably positioned towards a joint 76 that movably couples the upper part 62 and lower part 64 together. During the magnet removal process, the joint 76 is configured to hold the lower part 64 substantially parallel to the upper part 62, while allowing the actuation of the upper and lower parts 62, 64 towards one another.

In some embodiments, all or part of the lower part 64 (e.g., the magnet socket 68) may be formed from a ferromagnetic material so that the magnet 26 may be mechanically and magnetically held in place in the magnet socket 68 during the tool insertion and magnet removal processes. All or part of removal tool 60 may be formed from appropriate materials, e.g., surgical grade stainless steels.

Although various exemplary embodiments of the invention have been disclosed, it should be apparent to those skilled in the art that various changes and modifications can be made which will achieve some of the advantages of the invention without departing from the true scope of the invention.

What is claimed is:

1. A magnet insertion tool for use with an implantable device, the tool comprising:
   an upper part including an insertion member and an alignment member movably coupled to the insertion member, the insertion member having
      a positioning surface configured to position the implantable device between the insertion and alignment members,
      a magnet socket extending from the positioning surface and configured to hold an implant magnet, and
      an alignment surface configured to align the implantable device relative to the magnet socket,
      the alignment member having an engagement surface configured to engage the implantable device during insertion of the implant magnet, the alignment member configured to contact a portion of the insertion member such that the engagement surface and the positioning surface are spaced apart from one another; and
   a lower part movably coupled to the upper part, the lower part including a platform that is configured to move within the magnet socket from a bottom of the magnet socket to a top of the magnet socket during the insertion of the implant magnet so that the implant magnet moves within the magnet socket towards the alignment member.

2. The magnet insertion tool of claim 1, wherein the alignment member further includes a centering element configured to align the implantable device relative to the magnet socket.

3. The magnet insertion tool of claim 2, wherein the centering element has a ring shape.

4. The magnet insertion tool of claim 1, wherein at least a portion of the insertion member is formed from a ferromagnetic material configured to magnetically hold the implant magnet in the magnet socket.

5. The magnet insertion tool of claim 1, further comprising a spring between the upper and lower parts, the spring configured to hold the lower part so that the platform is biased toward a bottom of the magnet socket.

6. The magnet insertion tool of claim 5, wherein the spring is a flat spring.

7. The magnet insertion tool of claim 1, wherein the engagement surface and the positioning surface are spaced apart by a distance that permits the implantable device to be inserted between the engagement surface and the positioning surface.

8. The magnet insertion tool of claim 1, wherein the lower part is configured to contact the insertion member when the platform moves to the top of the magnet socket in order to prevent the platform from further upward movement within the magnet socket.

9. The magnet insertion tool of claim 1, wherein the lower part is movably coupled to the insertion member.

10. The magnet insertion tool of claim 9, wherein the alignment member is movably coupled to a middle section of the insertion member.

11. The magnet insertion tool of claim 1, wherein the insertion member includes a securing device configured to hold the insertion member and the alignment member together.

12. The magnet insertion tool of claim 11, wherein the alignment member includes a pin and the securing device is a latch configured to engage the pin.

13. The magnet insertion tool of claim 1, wherein the insertion member includes a tip configured to lift the implantable device so that the implantable device is positioned between the alignment and insertion members.

14. The magnet insertion tool of claim 1, wherein the alignment surface has a curved shape.

15. The magnet insertion tool of claim 1, wherein the upper and lower parts are movably coupled by a joint configured to hold the lower part substantially parallel to the upper part and configured to allow the lower part to move relative to the upper part by up to 90 degrees.

* * * * *